United States Patent [19]

Almeida

[11] E Re. 30,501

[45] Reissued Feb. 3, 1981

[54] UNIVERSAL KNEE ORTHOSIS

[76] Inventor: Manuel J. Almeida, 20 Ferreira Dr., Tiverton, R.I. 02878

[21] Appl. No.: 80,706

[22] Filed: Oct. 1, 1979

Related U.S. Patent Documents

Reissue of:

[64] Patent No.: 4,139,002
Issued: Feb. 13, 1979
Appl. No.: 832,425
Filed: Sep. 12, 1977

[51] Int. Cl.[3] ..... A61F 3/00

[52] U.S. Cl. ..... 128/80 C; 128/88; 2/22

[58] Field of Search ..... 128/80 C, 80 R, 80 F, 128/87 R, 88, 85, 165; 2/22

[56] References Cited

U.S. PATENT DOCUMENTS

| | | | |
|---|---|---|---|
| 412,213 | 10/1889 | Turner | 128/85 |
| 859,962 | 7/1907 | Messersmith | 128/88 |
| 3,528,412 | 9/1970 | McDavid | 128/80 C |
| 3,898,697 | 8/1975 | Whitehead | 2/22 |

FOREIGN PATENT DOCUMENTS

| | | | |
|---|---|---|---|
| 1236669 | 6/1960 | France | 128/80 F |

*Primary Examiner*—John D. Yasko
*Attorney, Agent, or Firm*—Salter & Michaelson

[57] ABSTRACT

A knee brace or orthosis for preventing hyperextension of the wearer's leg. In an additional embodiment the flexion of the wearer's leg is also regulated between positions permitting limited motion and a position wherein the knee is fixed and no motion is permitted. In its simplest form the orthosis includes upper and lower forward members and a rear member to which the upper and lower forward members are independently and pivotally attached. The forward rotational movement of the forward upper member is limited by abutting contact between opposed edges of the forward members, thus preventing rearward bending or hyperextension of the leg while permitting flexion. In the alternate embodiment, an upper rear member is provided and includes means for contacting upper portions of the rear member so as to limit flexion movement. In both cases the members are formed from relatively thin lightweight plastic material which has been at least partially shaped to custom conform to the dimensions of the wearer's leg.

14 Claims, 6 Drawing Figures

UNIVERSAL KNEE ORTHOSIS

Matter enclosed in heavy brackets [ ] appears in the original patent but forms no part of this reissue specification; matter printed in italics indicates the additions made by reissue.

BACKGROUND OF THE INVENTION

This invention relates to a brace or orthosis particularly adapted for use for controlling or supporting the movement of a patient's leg, but also has utility in regard to other joints such as the elbow. Conventional braces utilized to support a patient's leg either after operations or during other treatment have normally been fabricated of metal materials and extend from the hip to the bottom of the leg, special shoes being provided for securing the bottom of the braces. Such braces are heavy and cumbersome and accordingly cannot be used by patients who cannot support the weight involved such as children or frail persons. They are furthermore awkward in appearance and of constructions which are obvious to those observing the wearer.

Accordingly some attempts have been made to formulate at least portions of braces from relatively lightweight plastic material and to hingedly connect those portions together so as to provide a better leg brace. Generally such constructions utilize a single upper and a single lower member which are joined together by a pivot pin at a single hinge point. U.S. Pat. No. 3,575,166 to Roseman is illustrative of one such construction as is U.S. Pat. No. 3,528,412 to McDavid. The latter patent includes an upper member 10 joined to a lower member 12 at a pivot joint 14. A still further patent which shows a somewhat different brace construction is that to Whitehead, U.S. Pat. No. 3,898,697 which shows knee protection gear which has an upper member that is generally cylindrical and is pivotally connected to a lower member of somewhat similar configuration as best shown in FIGS. 4 and 5. The above citation and discussion of the above-indicated U.S. patents constitute applicant's Prior Art Disclosure.

SUMMARY OF THE INVENTION

Despite the availability of the constructions of the above-indicated types, there remains a need for a lightweight orthosis, the component parts of which may be fabricated to correspond to the wearer's leg dimensions and accordingly is comfortable for use. There is also a need of an orthosis which in addition to preventing hyperextension of the leg also permits varying degrees of flexion movement thereof in a comfortable and natural manner.

It is accordingly a primary object of the present invention to provide an orthosis which prevents hyperextension of the wearer's limb in a positive and relatively uncomplicated manner and which enables varying degrees of flexion movement.

A further object of the present invention is the provision of an orthosis, the component parts of which are custom fabricated to fit various portions of the wearer's limb with which they are adapted to contact in use, and which parts may be pivotally interconnected in such a manner that they prevent hyperextension of the wearer's limb, yet permit flexion movement thereof in varying degrees.

A still further object of the present invention is the provision of an orthosis of the immediately above-described type in which in addition to preventing hyperextension movement of the limb, may additionally prevent flexion movement thereof.

These and other objects of the present invention are accomplished by an orthosis which in its simplest embodiment includes separate forward upper and lower members and a rear member, wherein such forward members are independently pivotally connected to the rear member in such a fashion that they present edge surfaces which contact each other in abutting relationship to form a first stop means so as to prevent hyperextension of the limb. In an alternate embodiment the orthosis is provided with an upper rear member independently connected to the upper forward member and adapted to move upon attempted flexion motion of the limb into abutting contact with the rear member so as to form a second stop means whereby flexion movement of the limb is limited. The second stop means is releasable to the extent that it may be overriden so as to permit flexion movement of the limb when desired.

Other objects, features and advantages of the invention shall become apparent as the description thereof proceeds when considered in connection with the accompanying illustrative drawings.

DESCRIPTION OF THE DRAWING

In the drawing which illustrates the best mode presently contemplated for carrying out the present invention.

DESCRIPTION OF THE INVENTION

Figure 1:
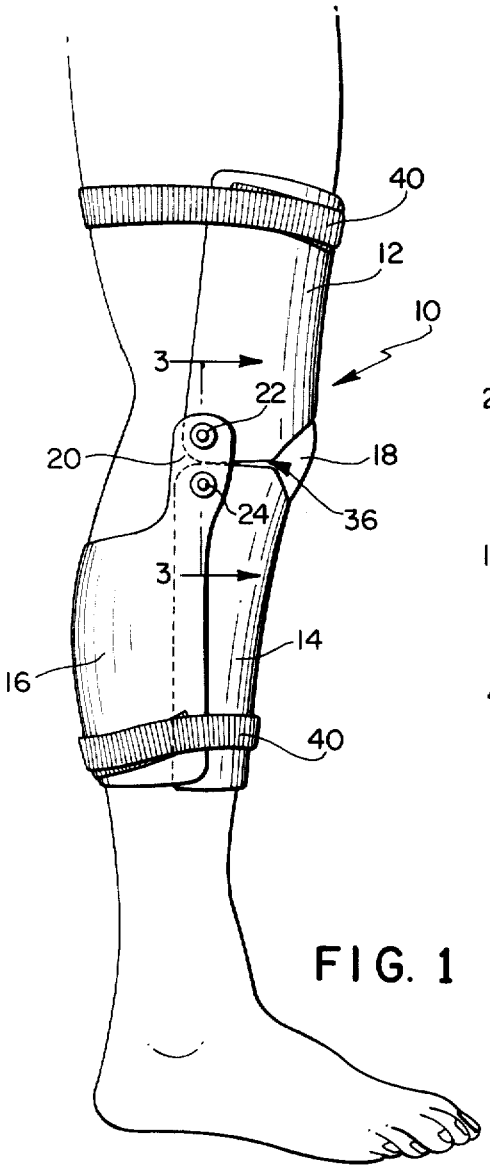
FIG. 1 is an elevational view of an orthosis embodied in the present invention as positioned upon the leg of a wearer.
Figure 2:
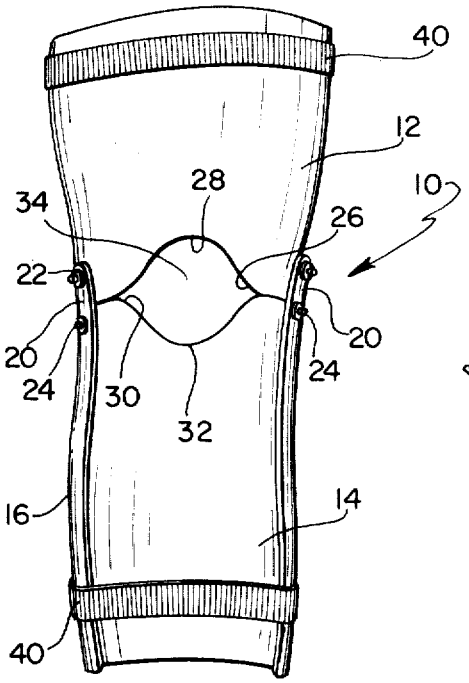
FIG. 2 is a front view of the orthosis shown in FIG. 1.
Figure 3:
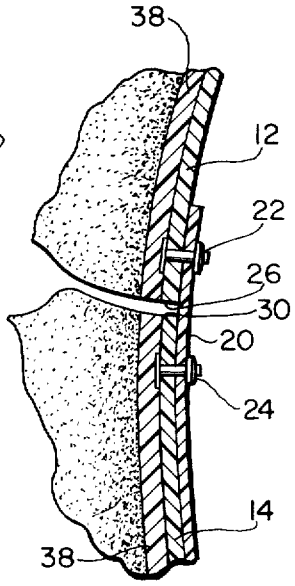
FIG. 3 is a partial sectional view taken along the line 3—3 of FIG. 1.

Referring now to the drawing and particularly to FIGS. 1 through 4 thereof, an orthosis or brace generally indicated at 10 is illustrated. The brace 10 includes an anterior or upper forward member 12, a forward lower member 14 and a posterior or rear member 16. The members 12, 14 and 16 are preferably formed from a lightweight relatively thin plastic material and are preferably molded about a cast or model of a person's leg so as to insure a comfortable and correct fit with those portions of the person's leg with which the members are adapted to engage when in operable position. The rear member 16 generally is positioned below the knee 18 of the wearer, and includes a pair of upwardly extending opposed ear portions 20. Both of the forward members 12 and 14 are independently hingedly connected to the ear portions 20 for at least limited pivotal movement with respect to each other. In some cases, however, it is desirable to utilize a rear member which extends upwardly above the knee and accordingly contacts both calf and thigh portions of the wearer, as in those cases where flexion movement is not required or desired to be imparted in the brace 10. As shown in FIG. 1, the ears 20 extend to a point upwardly on the wearer's leg adjacent or slightly above the knee 18. The upper forward member 12 is connected to the ears 20 by a pair of rivets 22 at points generally in line with the anatomical center of the knee 18. Similarly the lower member 14 is hingedly connected to the ears 20 by means of rivets 24 at a position adjacent to or slightly below the central portion of the knee 18.

The lower edge 26 of the upper forward member 12 is provided with an upwardly extending central cut-out portion 28, and the upper edge 30 of the lower member 14 is provided with a similar but downwardly extending cut-out portion 32. The cut-out portions 28, 32 are positioned in opposed relationship to each other and cooperatively form an opening 34 for receipt of the outwardly projecting portion of the wearer's knee. Furthermore the opposed edges 26 and 30 of the upper and lower forward members 12 and 14 respectively, are adapted to contact each other in abutting relationship and thereby define a stop 36. The stop 36 is generally operative when the wearer's leg is fully extended and thus prevents further forward pivotal movement of the upper member 12 with respect to the lower member 14 and the remaining portions of the brace. Accordingly, the stop 36 serves to prevent the wearer's leg from bending backward or i.e. preventing hyperextension.

Figure 4:
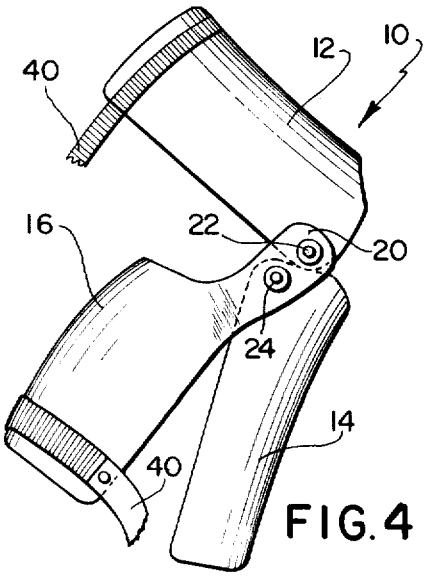
FIG. 4 is an elevational view of the orthosis showing the various members thereof pivoted apart from each other in a position to facilitate the donning of the orthosis upon the wearer's leg.

The inside of each of the brace members is provided with a relatively soft fabric or sponge material such as padding 38 for adding to the comfort of the brace 10. Furthermore the upper forward member 12 is positioned on the wearer's thigh by means of an upper strap 40 having a Velcro type fastener incorporated therein. Similarly the lower members 14 and 16 generally serve to envelop the calf portion of the wearer's leg and are maintained in such position by a lower nonelastic strap 40 that includes a Velcro fastener. In addition to the top member 12 being pivotal relative the remaining portion of the brace 10 in a forward direction simulating flexion movement of the leg, the lower portions of the lower members 14 and 16 are further pivotally moveable away from each other so as to enlarge the spacing therebetween to accommodate the wearer's foot as when donning the brace 10. Such disposition of the various parts to facilitate placing the brace in position on the wearer's leg is best shown in FIG. 4.

Figure 6:
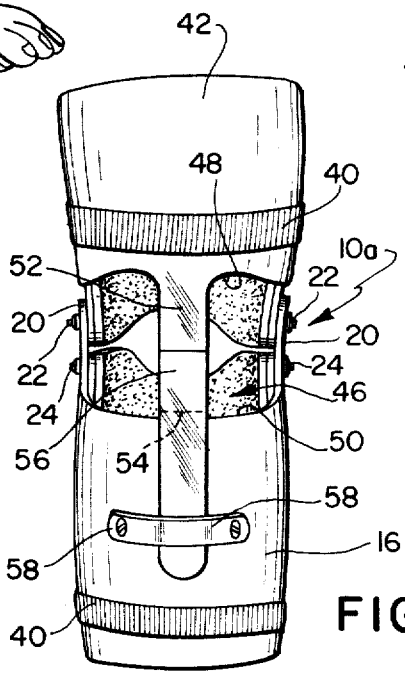
FIG. 6 is a posterior or rear view of the alternate orthosis construction shown in FIG. 5.
Figure 5:
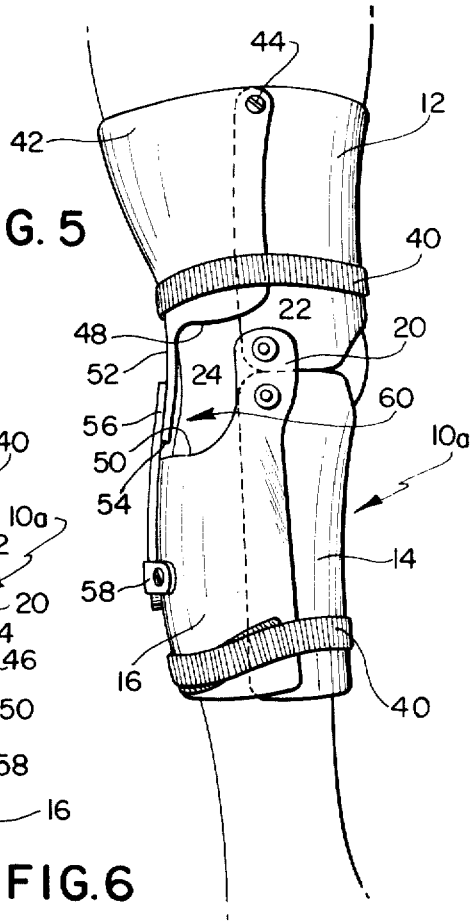
FIG. 5 is an elevational view similar to FIG. 1 but showing an alternate form of orthosis.

Referring now to FIGS. 5 and 6, an alternate form of the brace is generally indicated at 10a and as shown is similar in construction to the brace 10 illustrated in FIGS. 1 through 4. However, the brace 10a further includes an upper rear member 42 which is pivotally connected to the upper forward member 12 at the upper edge thereof by means of a pair of rivets 44. Accordingly the upper members 12 and 42 serve to envelop the upper or thigh portion of the wearer's leg and such disposition is maintained by a nonelastic strap 40 located proximal the lower portions thereof, that is, those portions that are moveable apart from each other. The rear central portion of the brace 10a is provided with an enlarged opening 46 formed between a lower edge 48 of the upper rear member 42 and an upper edge 50 of the rear member 16. Formed integral with the upper rear member 42 and extending downwardly from the lower edge 48 thereof is an extension 52. The lower edge or terminus 54 of such extension 52 is positioned slightly above or in abutting contact relative to the upper edge 50 of the rear member 16 when the wearer's leg is in approximately a fully extended position as shown in FIG. 6.

As shown in FIG. 5, a slide portion 56 is joined to the extension 52 by an adhesive or rivets (not shown) and extends downwardly therefrom for sliding contact with rear portions of the rear member 16. The lower portion of the slide 56 is received within a rigid plastic slide retainer 58 that is also suitably secured to the rear member 16 by adhesive or a rivet connection. Accordingly it is seen that when the slide 56 is in intimate contact with the rear member 16 as when the slide is positioned within the slide retainer or strap 58, the lower edge 54 of the extension 52 will abut the upper edge 50 of the lower member 16 should the wearer attempt further flexion movement of the knee. Accordingly the above-indicated cooperative structure forms a second stop means generally indicated at 60, wherein flexion movement of the knee as well as hyperextension thereof is prevented. However, should a wearer desire to override the second stop means 60, he can simply reach in back of the brace 10a and outwardly or rearwardly displace the extension 52 relative to the rear member 16, so as to permit the terminal edge 54 to ride downwardly against the rear portion of the rear member 16, whereupon flexion movement of the wearer's knee is permitted as for example when the wearer desires to move from a standing to a sitting position or for walking. Generally the slide 56 and the extension are formed of plastic material and accordingly the frictional movement therebetween is slight so as to permit necessary relative movement to accommodate flexion. If the slide retainer 58 is formed of an elastic material, it also continually forces the slide 56 against the rear member 16 so as to assure that the second stop is not inadvertently overridden. However, in some cases it is desirable to lock the knee in an immobile position, and in such cases the plastic slide retainer 58 may be secured to the rear member 16 adjacent to the upper edge 50 so that relative movement of the slide 56 as locked in the slide retainer 58 is prevented. In this instance the lower edge 54 substantially abuts the upper edge 50. If any flexion movement is required, the lowermost end of the extension 52 is cut away to define a space between the lower edge 54 and upper edge 50 as illustrated in FIG. 5. It is also contemplated that the device be formed without stops so as to provide medial and/or lateral stability for the knee on which the brace is mounted.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. An orthosis for the knee or elbow joint of a limb comprising, an upper forward member, a lower forward member and a rear member, means for positioning said upper member to said limb above said joint, and means for positioning said lower forward member and said rear member to said limb below said joint, both said forward members being independently hinged to said rear member for separate pivotal motion with respect to said rear member, said upper and lower forward members being further positioned respectively above and below said joint and cooperatively forming an opening for receipt of said joint, said upper forward member being limited in its forward pivotal movement by abutting contact between the upper edge of said lower forward member and the lower edge of said upper forward member, said abutting edges defining a stop so as to prevent hyperextension of said joint.

2. The orthosis of claim 1, said joint opening being formed by opposed cut-out portions that are formed in said abutting edges.

3. The orthosis of claim 1, said rear member being positioned on the back of said limb below said joint, said rear member having opposed ear portions upwardly extending at least laterally coextensive with said joint, at least said upper forward member being hingedly connected to said ears.

4. The orthosis of claim 3, both said forward members being hingedly connected to said ears.

5. The orthosis of claim 1, said upper forward member being freely rearwardly pivotal about said rear member to permit flexion movement of said joint.

6. The orthosis of claim 5, each of said members being formed of a relatively thin-wall plastic material that is preshaped for fitting with the respective limb portions in contact therewith, said lower forward member and said rear member cooperatively and circumferentially enveloping the lower portion of said limb.

7. The orthosis of claim 1, said limb being a leg, said lower forward member and said rear member being pivotal outwardly apart from each other at respective lower portions thereof for receipt of the foot portion of said leg in donning said orthosis.

8. The orthosis of claim 1, said rear member being a lower rear member, there further being an upper rear member connected to said upper forward member, said upper rear member having means downwardly extending from rear portions thereof for contacting said rear member so as to prevent flexion movement of said joint.

9. The orthosis of claim 8, said flexion preventing means being a stop adapted to contact the upper edge of said rear member.

10. The orthosis of claim 9, said stop including a first segment extending downwardly from said upper rear member, said first segment terminating in a lower edge for abutting the upper edge of said rear member, and a second segment in the form of a slide that is connected to said first segment and forming a downward extension thereof, said slide being receivable in a slide retainer that is positioned on said rear member below the upper edge thereof.

11. The orthosis of claim 10, said slide retainer permitting limited longitudinal motion of said slide relative to said rear member to permit limited flexion of said joint.

12. The orthosis of claim 10, said slide retainer urging said slide continually inwardly against said lower member, and subsequently urging said stop against said lower member upper edge, thereby permitting essentially no flexion joint movement.

*13. An orthosis for the knee or elbow joint of a limb comprising, an upper forward member, a lower forward member and a rear member, means for locating said upper forward member on said limb above said joint, means for locating said lower forward member and said rear member on said limb below said joint, said lower forward member being hingedly connected to said rear member for independent pivotal motion with respect thereto, and said upper and lower forward members being positioned respectively above and below said joint and being formed with cut-out portions to cooperatively form an opening for receiving said joint therein.*

*14. An orthosis of claim 13, said upper forward member being hingedly connected to said rear member for independent pivotal motion with respect thereto and said lower forward member.*

* * * * *